United States Patent [19]

Robert

[11] 4,212,884
[45] Jul. 15, 1980

[54] PREVENTION OF PROSTAGLANDIN-INDUCED ENTEROPOOLING WITH PGI'S AND PGD'S

[75] Inventor: Andre' Robert, Kalamazoo, Mich.

[73] Assignee: The Upjohn Company, Kalamazoo, Mich.

[21] Appl. No.: 9,216

[22] Filed: Feb. 5, 1979

Related U.S. Application Data

[63] Continuation-in-part of Ser. No. 905,481, May 12, 1978, abandoned.

[51] Int. Cl.$^2$ .................... A61K 31/19; A61K 31/34; A61K 31/215
[52] U.S. Cl. .................................. 424/285; 424/305; 424/317
[58] Field of Search .................... 424/305, 317, 285

[56] References Cited

U.S. PATENT DOCUMENTS 4,070,482  1/1978  Lippmann et al. .................. 424/317

OTHER PUBLICATIONS

Schaaf et al. Chem. Abst. vol. 80 (1974) p. 145554v.

*Primary Examiner*—Stanley J. Friedman
*Attorney, Agent, or Firm*—Robert A. Armitage

[57] ABSTRACT

The present invention relates to a method for the inhibition of the diarrheogenic effects of prostaglandin administration and consists of the concommitant administration with a diarrheogenic prostaglandin of an anti-enteropooling dose of an 11-oxo-prostaglandin or a prostacyclin.

6 Claims, No Drawings

PREVENTION OF PROSTAGLANDIN-INDUCED ENTEROPOOLING WITH PGI'S AND PGD'S

DESCRIPTION

Method

CROSS REFERENCE TO RELATED APPLICATIONS

This application is a continuation-in-part of Ser. No. 905,481, filed May 12, 1978, now abandoned.

TECHNICAL FIELD

When used for numerous therapeutic indications, various prostaglandins known in the art have a recognized diarrheogenic potential. This potential for the induction of diarrhea for a given prostaglandin is readily and efficiently assessed by its ability to cause the accumulation of fluid in the small intestine of standard laboratory animals treated with the prostaglandin. This phenomenon of fluid accumulation, referred to as enteropooling, is quantitatively determined by methods known in the art. See, for example, Robert, A., et al., Prostaglandins, 11:809-828 (1976).

As used herein, the term prostaglandins refers to members of that family of naturally-occurring fatty acids (such as $PGE_2$ and $PGF_{2\alpha}$), as well as the various chemical analogs thereof known in the art. Among those prostaglandin analogs known in the art there are the PGC-type compounds of U.S. Pat. No. 3,993,686; the 9-deoxy-9-methylene -PGF-type compounds of U.S. Pat. Nos. 4,021,467 and 4,060,534; the 11-deoxy-PG-type compounds of U.S. Patents 4,029,693 and 3,987,072; the $8\beta,12\alpha$-PG-type compounds of U.S. Pat. No. 3,979,483; the 2,2-di-fluoro-PG-type compounds of U.S. Pat. No. 4,001,300; the cis-4,5-didehydro-PG-type compounds of U.S. Pat. Nos. 4,032,561 and 3,933,889; the inter-phenylene-PG-type compounds of U.S. Pat. Nos. 4,020,097 and 3,997,566; the 5,6-didehydro-$PG_2$-type or 4,4,5,5-tetrade-hydro-$PG_1$-type compounds of U.S. Pat. No. 4,013,695; the 5-oxa-$PG_1$-type compounds of U.S. Pat. Nos. 3,931,279 and 3,864,387; the 4-oxa-$PG_1$-type and 3-oxa-$PG_1$-type compounds of U.S. Pat. No. 3,944,593; the 13-cis-PG-type compounds of U.S. Pat. No. 4,026,909; the 13,14-didehydro-PG-type compounds of U.S. Pat. Nos. 4,029,681 and 4,018,803; the $\omega$-aryl-PG-type compounds of U.S. Pat. No. 3,987,087; the 107-aryloxy-PG-type compounds of U.S. Pat. No. 3,864,387; the 16-alkyl-PG-type compounds of U.S. Pat. No. 3,903,131; the 16-fluoro-PG-type compounds of U.S. Pat. No. 3,962,293; and 15-methyl-PG-type compounds of U.S. Pat. No. 3,728,382.

While the naturally-occurring prostaglandins are carboxylic acids, numerous derivatives thereof are known in the art. For example, ester derivatives, including especially aromatic and phenacyl esters, are known in the art. See U.S. Pat. Nos. 3,069,332, 3,598,858, 3,979,440, and 3,984,062. Likewise, salts of these carboxylic acids are known in the art. See U.S. Pat. Nos. 3,069,332 and 3,958,858 cited above, as well as other references such as U.S. Pat. Nos. 3,657,327 and 3,888,916. Other derivatives of the prostaglandins, such as the amides thereof, are known in the art. See U.S. Pat. Nos. 3,853,941, 3,884,942, 3,903,299, 3,880,883, and 3,953,470.

Finally, there are also known macrocyclic lactone derivatives of the prostagandins as is, for example, described by Corey, E. J., et al., JACS 97:653 (1975) and U.S. Pat. Nos. 3,931,206, 4,067,991, 4,049,648, 4,032,543, 4,045,449, and 4,049,678.

In addition to these various carbonyl-containing prostaglandin analogs, there are likewise known in the art acidic, non-carboxylic prostaglandin analogs such as tetrazoles and sulfonates. See for example the 2-decarboxy-2-tetrazolyl-PG analogs described in U.S. Pat. Nos. 3,883,513, 3,932,389, 3,984,400, and 4,035,360. Also 2-decarboxy-2-2-sulfonyl-type compounds are described in U.S. Pat. No. 3,922,301.

Among the various other modifications at the C-2 position of the known prostaglandin analogs is the replacement of the carboxyl with an amine, as is for example described in U.S. Pat. No. 4,073,808 and Derwent Farmdoc CPI No. 46957Y (abstracting Belgian Patent No. 849,963).

Numerous references also describe primary alcohols corresponding to the known prostaglandins and analogs thereof as are described in U.S. Pat. Nos. 4,028,419, 4,055,602, 4,032,576, 3,931,207, 3,878,239, 3,966,792, 4,024,174, 3,962,312, 3,636,120, 3,723,528, 3,895,058, 3,954,881, 4,004,021, and 3,962,218. In addition to these 2-decarboxy-2-hydroxymethyl-PG compounds, there are known the corresponding C-2 aldehydes as described in U.S. Pat. Nos. 3,931,296 and 3,953,435. See also Derwent Farmdoc CPI No. 35953X and 93049X for a description of further 2-decarboxy-2-carboxaldehyde-PG analogs. Finally, the C-2 acetals thereof are described at Derwent Farmdoc CPI No. 94924X.

There are further known in the art 11-oxo-prostaglandins, notably PGD-type, $9\beta$-PGD-type, 9-deoxy-PGD-type, 9-deoxy-9,10-didehydro-PGD-type, and the corresponding 12,13-didehydro analogs thereof. These 11-oxo-prostaglandins are described in U.S. Pat. No. 4,016,184.

In addition to the various prostaglandins, including prostaglandin analogs and 11-oxo-prostaglandins known in the art, there are further known the prostacyclins. As that term is used herein, the term prostacyclins refers not only to prostacyclin or $PGI_2$ itself, but various, and notably more stable, analogs thereof.

Prostacyclin is an unsaturated heterocyclic carboxylic acid and its preparation and certain of its pharmacological uses are described in Belgian Pat. No. 851,122 (published as Derwent Farmdoc CPI No. 57511Y) and Belgian Pat. No. 854,463 (published as Derwent Farmdoc CPI No. 81213Y). Among the analogs of prostacyclin are the 5,6-dihydro-$PGI_1$ compounds, described in Belgian Pat. No. 855,224 (published as Derwent Farmdoc CPI No. 86540Y); the 9-thia analog of prostacyclin, described at JACS 99:7734 (1977); the 4,5-didehydro-$PGI_1$ compound, described at JCS Chem. Comm. 1977:331-332 and JACS 99:2006-2008 (1977) and U.S. Pat. No. 4,109,082; the C-9 nitrogen analogs of prostacyclin, described in U.S. Pat. No. 4,097,489; the 5-hydroxy-$PGI_1$ compounds, described in U.S. Pat. No. 4,110,532; the 4-oxo-$PGI_1$ compounds, described in U.S. Pat. No. 4,126,744; the 7,8-didehydro-$PGI_1$ compounds, described in U.S. Ser. No. 869,141 (filed Jan. 13, 1978); the 6,7-didehydro-$PGI_1$ compounds, described in U.S. Pat. No. 4,128,713; the carbocyclic analogs of prostacyclin, described in U.S. Ser. No. 877,253 (filed Feb. 13, 1978); the C-5 isomers of prostacyclin, described in U.S. Ser. No. 775,003 (filed Mar. 7, 1977); the 9-deoxy-9-hydroxymethylene -$PGI_1$ compounds, described in U.S. Pat. No. 4,130,569; and the 7a-homo- PGI₁ compounds, described in U.S. Ser. No. 904,781 (filed May 11, 1978).

SUMMARY OF THE INVENTION

The present invention relates to a novel method for the pharmacologic use of prostacyclins and 11-oxo-prostaglandins.

The present invention further provides an improved method by which diarrheogenic prostaglandins are used for pharmacological purposes.

The present invention further provides a method whereby the undesirable gastrointestinal side effects of diarrheogenic prostaglandins are minimized or eliminated.

In particular, the present invention provides in a method consisting of administering a diarrheogenic prostaglandin systemically to a mammal for the induction of a prostaglandin-like pharmacological effect, an improvement which comprises:

concommitantly administering an anti-enteropooling dose of a prostacyclin or 11-oxo-prostaglandins.

The prostaglandins are known in the art as useful pharmacological agents for a wide variety of purposes. In particular, prostaglandins are known to be useful for obstetric and gynecological purposes, including abortion, menstrual regulations, and labor induction. Further, certain of the prostaglandins (particularly the PGE-type compounds) are useful in lowering mammalian blood pressure. Other pharmacological effects of the prostaglandins include reduction of gastric secretion (facilitating healing of gastric and duodenal ulcers), blood platelet aggregation inhibition (reducing the possibility of thrombosis), and bronchodilation (e.g., anti-asthmatic uses). For examples of the numerous pharmacological effects induced by the prostaglandins, see the various references provided above describing various prostaglandins, including their analogs.

A further characteristic of the prostaglandins is their ability to stimulate smooth muscle, notably gastrointestinal smooth muscle. Further, many of the prostaglandins, exhibiting an otherwise highly desirable pharmacological profile of activity, cause enteropooling or the collection of substantial quantities of fluid in the intestine. This accumulation of fluid in the intestine, together with the stimulation of gastrointestinal smooth muscle which causes fluid transit in the gastrointestinal tract, is responsible for the diarrhea, especially watery diarrhea, associated with prostaglandin administration in many patients and animals.

For the purposes of the present invention, diarrheogenic prostaglandins are considered to be any prostaglandins, which cause diarrhea in the rat at therapeutic doses as a result of their potency in the rat enteropooling assay described in Robert, A., et al., Prostaglandins 11:809-828 (1976). Accordingly, the diarrheogenic prostaglandins include prostaglandins such as $PGE_2$, $PGA_1$, $PGA_2$, and $PGB_2$; as well as analogs such as 16,16-dimethyl-$PGE_2$, 15-methyl-$PGE_2$, 15-epi-15-methyl-$PGE_2$, 15-methyl-$PGE_2$, -methyl-$PGF_2\beta$, and 15-epi-15-methyl-$PGF_2\beta$. In accordance with this definition of diarrheogenic prostaglandins, the compounds so defined are those which, when administered to humans or valuable domestic animals at therapeutic doses cause diarrhea as a side effect of the administration thereof.

The improvement of the present invention comprises, as indicated above, the administration of a prostacyclin or an 11-oxo-prostaglandin. As indicated above, the term prostacyclin and the term 11-oxo-prostaglandin refer to compounds whose preparation and formulation for pharmacological purposes is described in the references cited above. For example, these references describe the importance of certain prostacyclins and the 11-oxo-prostaglandins as platelet aggregation inhibitors, thus rendering such compounds potent antithrombotic agents. The present invention comprises, however, the further discovery that the 11-oxo-prostaglandins and rostacyclins are further characterized by an ability to inhibit the enteropooling effects of the diarrheogenic prostaglandins. Accordingly, this further pharmacologic property renders the prostacyclins and 11-oxo-prostaglandins useful in accordance with the present method.

The prostacyclin or 11-oxo-prostaglandin is administered at an anti-enteropooling dose in accordance with the present invention. Depending upon the incidence and extent of diarrhea encountered with the diarrheogenic prostaglandin being concommitantly administered, an anti-enteropooling dose of the prostacyclin or 11-oxo-prostaglandin is employed to reduce the amount of fluid accumulated in the intestine from 50% ($ED_{50}$) to 100% ($ED_{100}$). In determining the amount of prostacyclin or 11-oxo-prostaglandin sufficient to result in the desired diminution of enteropooling, firstly the relative potency of the particular prostacyclin or 11-oxo-prostaglandin is determined.

This relative potency is determined by readily available experimental techniques. Accordingly, the rat enteropooling assay as described by A. Robert is undertaken, but with the modification that the rats treated with the diarrheogenic prostaglandin are divided into two groups, a control group and a group concommitantly treated with either the prostacyclin or 11-oxo-prostaglandin. For convenience, subcutaneous dosages of the prostacyclin or 11-oxo-prostaglandin are given. Further the prostacyclin or 11-oxo-prostaglandin is given about 10 minutes prior to the administration of the diarrheogenic prostaglandin. By this method the decrease in enteropooling obtained by treatment with the prostacyclin or 11-oxo-prostaglandin is readily determined. Further the reduction in enteropooling in animals treated with the prostacyclin or 11-oxo-prostaglandin will be dose dependent, thus permitting a determination of the $ED_{50}$ and $ED_{100}$ values which are used in determining relative potency.

For example, by the procedure described above the anti-enteropooling $ED_{50}$ of prostacyclin (or $PGI_2$) is 15 μg/kg subcutaneously when a 100 μg/kg oral dose of 16,16-dimethyl-$PGE_2$ is administered 10 minutes after treatment with $PGI_2$. Moreover the anti-enteropooling $ED_{50}$ for $PGI_2$ is substantially independent of the dosage of 16,16-dimethyl-$PGE_2$, being an effective inhibitor of enteropooling with doses from 0.5-1000 μg/kg orally of 16,16-dimethyl-$PGE_2$.

Thus, in accordance with the present invention an anti-enteropooling $ED_{50}$ or $ED_{100}$ is determined for each prostacyclin or 11-oxo-prostaglandin substantially independently of the dose of prostacyclin or 11-oxo-prostaglandin being employed therapeutically. Therefore the concomitant dose in accordance with the present invention is readily determined solely as a function of the relative anti-enteropooling potency of the prostacyclin or 11-oxo-prostaglandin. Thus for the purposes of the present invention dosages in the range of 0.1 μg/kg/day to 10 mg/kg/day will be efficacious as indicated above, with the exact dose depending on the potency and the route of administration.

Finally, the practice of the method according to the present invention requires the concommitant administration of the anti-enteropooling dose of prostacyclin or 11-oxo-prostaglandin with the diarrheogenic prostaglandin being employed for the induction of the prostaglandin-like pharmacological effect. For the purposes of the present invention, the concommitant administration refers to administration either slightly prior to or at the same time as the administration of the diarrheogenic prostaglandin and either by the same route or by any other route of administration. The attending physician or veterinarian can readily determine the desirability of either administration by the same or a different route according to the clinical or veterinary presentation and available knowledge regarding the stability and/or suitability of the prostacyclin or 11-oxo-prostaglandin for administration by a particular route being considered. Thus, for example, for compounds like prostacyclin, which are unstable in acidic media, oral administration is ordinarily avoided. In other instances, ease and simplicity of administration would provide a preference for the concommitant use of the diarrheogenic prostaglandin and prostacyclin or 11-oxo-prostaglandin by the same route of administration.

Finally, while the present invention relates to an improved method for the induction of prostaglandin-like pharmacological effects with diarrheogenic prostaglandin in mammals, the preferred embodiment of the present invention is its use in man. Other uses of the present method include, however, the use in valuable domestic animals such as cattle and pigs or canine, feline, or equine species.

I claim

1. In a method consisting essentially of administering a diarrheogenic prostaglandin systemically to a mammal for the induction of a prostaglandin-like pharmacological effect, an improvement which comprises:
concommitantly administering an anti-enteropooling dose of a prostacyclin or 11-oxo-prostaglandin.

2. An improvement according to claim 1, wherein said anti-enteropooling dose is at least the $ED_{50}$.

3. An improvement according to claim 1, wherein said diarrheogenic prostaglandin is 16,16-dimethyl-$PGE_2$.

4. An improvement according to claim 1, wherein said prostacyclin or 11-oxo-prostaglandin is $PGD_2$.

5. An improvement according to claim 1, wherein said prostacyclin or 11-oxo-prostaglandin is $PGI_2$.

6. An improvement according to claim 1, wherein said prostacyclin or 11-oxo-prostaglandin is $PGI_1$.

* * * * *

UNITED STATES PATENT OFFICE
CERTIFICATE OF CORRECTION

Patent No. 4,212,884                    Dated    15 July 1980

Inventor(s)   André Robert

It is certified that error appears in the above-identified patent and that said Letters Patent are hereby corrected as shown below:

Column 1, line 48, "the 107-aryloxy-PG-type" should read -- the ω-aryloxy-PG-type --;

Column 2, line 9, "2-decarboxy-2-2-sulfonyl-" should read -- 2-decarboxy-2-sulfonyl- --;

Column 3, line 59, "15-methyl-PGE$_2$, -methyl-PGF$_2$β, and" should read -- 15-methyl-PGF$_2$β, and --;

Column 4, line 10, "rostacyclins" should read -- prostacyclins --.

Signed and Sealed this

*Fourteenth* Day of *April 1981*

[SEAL]

Attest:

RENE D. TEGTMEYER

*Attesting Officer*    *Acting Commissioner of Patents and Trademarks*